US012680124B2

(12) United States Patent
Huang et al.

(10) Patent No.: US 12,680,124 B2
(45) Date of Patent: Jul. 14, 2026

(54) METHOD FOR DETECTION OF SPECIFIC NUCLEIC ACIDS

(71) Applicant: Siemens Healthcare GmbH, Erlangen (DE)

(72) Inventors: Yiwei Huang, Erlangen (DE); Tivadar Mach, Nuremberg (DE); Maximilian Würstle, Baiersdorf (DE); Stefan Prause, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 1346 days.

(21) Appl. No.: 17/291,792

(22) PCT Filed: Oct. 29, 2019

(86) PCT No.: PCT/EP2019/079475
§ 371 (c)(1),
(2) Date: May 6, 2021

(87) PCT Pub. No.: WO2020/094455
PCT Pub. Date: May 14, 2020

(65) Prior Publication Data
US 2021/0388421 A1     Dec. 16, 2021

(30) Foreign Application Priority Data
Nov. 7, 2018     (EP) ..................................... 18204788

(51) Int. Cl.
*C12Q 1/6816*     (2018.01)
*C12N 15/11*     (2006.01)
*C12Q 1/6804*     (2018.01)

(52) U.S. Cl.
CPC .......... *C12Q 1/6816* (2013.01); *C12N 15/111* (2013.01); *C12Q 1/6804* (2013.01); *C12N 2310/20* (2017.05)

(58) Field of Classification Search
CPC .. C12Q 1/6816; C12Q 1/6804; C12Q 1/6827; C12N 15/111; C12N 2310/20
See application file for complete search history.

(56) References Cited

U.S. PATENT DOCUMENTS

| | | | |
|---|---|---|---|
| 2012/0219941 A1 | 8/2012 | Shyamala | |
| 2015/0037797 A1 | 2/2015 | Kappel et al. | |
| 2017/0268035 A1 | 9/2017 | Singer et al. | |
| 2018/0340221 A1 | 11/2018 | Davis et al. | |

FOREIGN PATENT DOCUMENTS

| | | | |
|---|---|---|---|
| CA | 2803693 A1 | 3/2012 | |
| CN | 102660539 A | 9/2012 | |
| CN | 103080338 A | 5/2013 | |
| CN | 105177110 A | 12/2015 | |
| CN | 107208086 A | 9/2017 | |

| | | | | |
|---|---|---|---|---|
| CN | 108350489 A | 7/2018 | | |
| WO | WO 2017147345 A1 | 8/2017 | | |
| WO | 2017219027 A1 | 12/2017 | | |
| WO | WO-2018060740 A1 * | 4/2018 | ........... | C12Q 1/6869 |
| WO | WO 2018107129 A1 | 6/2018 | | |
| WO | WO 2018151339 A1 | 8/2018 | | |
| WO | WO-2018170340 A1 * | 9/2018 | ........... | C12N 15/115 |

OTHER PUBLICATIONS

Van Nostrand, Eric L., Stephanie C. Huelga, and Gene W. Yeo. "Experimental and computational considerations in the study of RNA-binding protein-RNA interactions." RNA Processing: Disease and Genome-wide Probing (2016): 1-28 . . . (Year: 2015).*
Weeks, Ian, et al. "Acridinium esters as high-specific-activity labels in immunoassay." Clinical chemistry 29.8 (1983): 1474-1479 . . . (Year: 1983).*
Adams, Nicholas M., et al. "Comparison of three magnetic bead surface functionalities for RNA extraction and detection." ACS applied materials & interfaces 7.11 (2015): 6062-6069 . . . (Year: 2015).*
Bell, Nicholas AW, and Ulrich F. Keyser. "Digitally encoded DNA nanostructures for multiplexed, single-molecule protein sensing with nanopores." Nature nanotechnology 11.7 (2016): 645-651. (Year: 2016).*
Hornbeck, Peter V. "Enzyme-linked immunosorbent assays." Current protocols in immunology 110.1 (2015): 2-1. (Year: 2015).*
"Advia Centaur XPT Immunoassay-System*"; Siemens; Webpage Snapshot (Nov. 9, 2018), 4 pages.
Advia Centaur XPT Immunoassay System, Technical Specification (Apr. 2017) , 2 pages.
"Atellica IM 1300 Analyzer and Atellica IM 1600 Analyzer" Technical Specifications (Apr. 2018).
"Atellica Solution Immunoassay Clinical Chemistry Analyzers"; Siemens; Webpage Snapshot (Nov. 9, 2018), 4 pages.

(Continued)

*Primary Examiner* — Ekaterina Poliakova-Georgantas
*Assistant Examiner* — John Charles Mckillop
(74) *Attorney, Agent, or Firm* — BakerHostetler

(57) ABSTRACT

The present invention relates to a method for detecting a target RNA polynucleotide by using a catcher polynucleotide which anneals to at least a portion of the target RNA polynucleotide, and a catalytically-inactive crRNA-guided (CRISPR RNA) RNA-binding protein which binds to the target RNA polynucleotide. Further envisaged is a kit for detecting a specific target RNA polynucleotide comprising inter alia one or more catcher polynucleotides complementary to at least a portion of the target RNA polynucleotide, a mature crRNA molecule which is specific for a target sequence on the target RNA polynucleotide and a catalytically-inactive crRNA-guided RNA-binding protein; as well as the use of these ingredients for the detection of the target RNA polynucleotide.

19 Claims, 1 Drawing Sheet
Specification includes a Sequence Listing.

(56)  References Cited

OTHER PUBLICATIONS

"Laboratory Procedure Manual: Complex PSA using Advia Centaur in Serum Nhanes 2007-2008" by University of Washington Medical Center, Department of Laboratory Medicine, Immunology Division.

Abudayyeh, Omar O. et al.: "C2c2 is a single-component programmable RNA-guided RNA-targeting CRISPR effector"; in: Science; vol. 353; Issue 6299; pp. 557; 2016.

Abudayyeh, Omar O. et al.: "RNA targeting with CRISPR-Cas13a"; in: Nature; vol. 550; pp. 280-284; 2017.

Bird, Robert E. and Walker, Barbara W.: "Single chain antibody variable regions"; in: Trends in Biotechnology; vol. 9; No. 1; pp. 132-137; 1991.

Cong, Le et al.: "Multiplex Genome Engineering Using CRISPR/ Cas Systems"; in: Science; vol. 339; pp. 819-823; 2013.

Cox, David B.T. et al.: "RNA editing with CRISPR-Cas13"; in: Science; vol. 358; No. 6366; pp. 1019-1027; 2017.

East-Seletsky et al: "Two distinct RNase activities of CRISPR-C2c2 enable guide-RNA processing and RNA detection", Nature, vol. 538, No. 7624, Sep. 26, 2016 (Sep. 26, 2016), pp. 270-273.

East-Seletsky, Alexandra et al.: "RNA Targeting by Functionally Orthogonal Type VI-A CRISPR-Cas Enzymes"; in: Molecular Cell; vol. 66; No. 3; pp. 373-383, 2017.

Gootenberg, Jonathan S. et al.: "Multiplexed and portable nucleic acid detection platform with Cas13, Cas12a, and Csm6"; in: Science; vol. 360; Issue 6387; pp. 439-444; 2018.

Granados-Riveron, Javier and Aquino-Jarquin, Guillermo.: "CRISPR-Cas13 Precision Transcriptome Engineering in Cancer"; in: Cancer Research; vol. 78; No. 15; pp. 4107-4113; 2018.

Hudson, Peter J. and Kortt, Alexander A.: "High avidity scFv multimers; diabodies and triabodies"; in: Journal of Immunological Methods; vol. 231; pp. 177-189; 1999.

Murugan, Karthik et al.: "The Revolution Continues: Newly Discovered Systems Expand the CRISPR-Cas Toolkit"; in: Molecular Cell Review; vol. 68; No. 1; pp. 15-25; 2017.

Quiocho, F.A.: "Making of the minibody"; in: Nature; vol. 362; pp. 293-294; 1993.

Sittampalam, Sitta G. et al., Ed., "Assay Guidance Manual"; by Bethesda (MD): Eli Lilly Company and the National Center for Advancing Translational Sciences; 2004—pdf divided into sections for upload.

Skerra, Arne and Plueckthun, Andreas.: "Assembly of a functional immunoglobulin Fv fragment in *Escherichia coli*"; in: Science; vol. 240; No. 4855; pp. 1038-1041; 1988.

Smargon, Aaron A. et al.: "Cas13b Is a Type VI-B CRISPR-Associated RNA-Guided RNase Differentially Regulated by Accessory Proteins Csx27 and Csx28"; in: Molecular Cell; vol. 65; No. 4; pp. 618-630; 2017.

Williams, Eli S. et al.: "Molecular Diagnosis of Human Disease"; in: Molecular Pathology; Chapter 30; pp. 691-707; 2018.

* cited by examiner

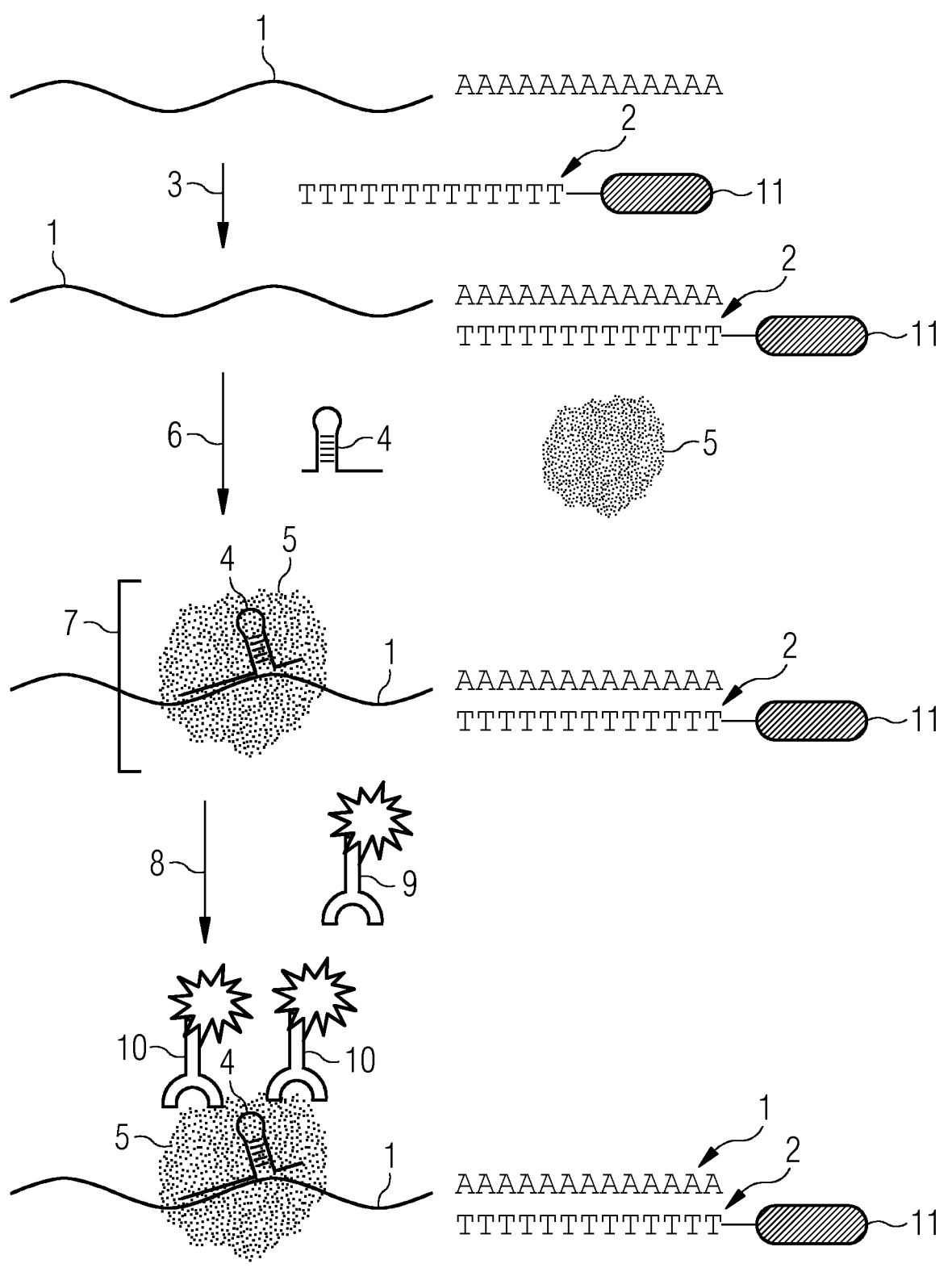

METHOD FOR DETECTION OF SPECIFIC NUCLEIC ACIDS

CROSS-REFERENCE TO RELATED APPLICATIONS

This application is a 35 U.S.C. § 371 national phase application of International Patent Application No. PCT/EP2019/079475, filed Oct. 29, 2019, which claims priority to EP Application No. 18204788.6, filed Nov. 7, 2018, the entire disclosure of each of which is incorporated herein by reference in its entirety.

SEQUENCE LISTING

This application contains a Sequence Listing which has been submitted electronically in ASCII format and is hereby incorporated by reference in its entirety. Said ASCII copy, created Jan. 8, 2025, is named 040677.000012_sequence-listing.txt and is 763 bytes in size.

TECHNICAL FIELD

The present invention relates to a method for detecting a target RNA polynucleotide by using a catcher polynucle-otide which anneals to at least a portion of the target RNA polynucleotide, and a catalytically-inactive crRNA-guided (CRISPR RNA) RNA-binding protein which binds to the target RNA polynucleotide. Further envisaged is a kit for detecting a specific target RNA polynucleotide comprising inter alia one or more catcher polynucleotides complementary to at least a portion of the target RNA polynucleotide, a mature crRNA molecule which is specific for a target sequence on the target RNA polynucleotide and a catalytically-inactive crRNA-guided RNA-binding protein; as well as the use of these ingredients for the detection of the target RNA polynucleotide.

BACKGROUND

The field of molecular diagnostics has become increasingly important in clinical laboratories. Various molecular diagnostic tests and assay are used in modern clinical applications, e.g. in the context of infectious diseases, oncological examinations, coagulation tests, pharmacogenetics, or the assessment of genetic disorders (Williams et al., Molecular Pathology 2018, 691-707). Molecular diagnostic testing is usually utilized to detect specific DNA or RNA sequences which are directly or indirectly associated with a disease, including single nucleotide polymorphisms (SNPs), deletions and insertions. Current techniques for detection or quantification of specific nucleic acid sequences include heterogeneous hybridization assays, PCR methods or direct sequencing.

The CRISPR/Cas-technology is a new and very versatile genome- and epigenome-editing tool based on repurposing the CRISPR/Cas (clustered regularly interspersed short palindromic repeats/Cas) bacterial immune system (Cong et al, 2013, Science, 339, 819-824). The Cas nuclease, when complexed with a short RNA oligonucleotide known as a single guide RNA (sgRNA), can induce double-stranded breaks (DSBs) at specific sgRNA complementary locations.

Recently, the CRISPR/Cas-technology was adapted to provide low-cost and practical diagnostic tools also for RNA targeting. In particular, type VI CRISPR-Cas systems such as the Cas13-based system are capable of binding to RNA polynucleotides when guided by suitable cRNA forms (Murugan et al., 2017, Mol Cell., 68(1), 15-25). An example of a Cas13-based approach is SHERLOCK (Specific High-Sensitivity Enzymatic Reporter UnLOCKing), a diagnostic tool capable of fast and sensitive detection of RNA in samples based on collateral cleavage of reporter release signals (Gootenberg et al., 2017, Science, 360, 6387, 439-444).

However, these approaches are confined to rather specific situations and do not exploit all diagnostic options provided by RNA-based CRISPR/Cas-system. Thus, there is a need for new and improved detection approaches, which allow for an efficient and accurate characterization of RNA polynucleotides.

SUMMARY

The present invention addresses this need and provides a method of detecting a target RNA polynucleotide comprising: (i) providing an RNA polynucleotide; (ii) annealing one or more catcher polynucleotides which are complementary to at least a portion of the target RNA polynucleotide to obtain a hybrid of said target RNA polynucleotide and said catcher polynucleotide, wherein said catcher nucleotide is immobilized on a surface or connected to a bead; (iii) annealing a mature crRNA (CRISPR RNA) molecule to a specific target sequence on the target RNA polynucleotide; (iv) binding a catalytically-inactive crRNA-guided RNA-binding protein to the complex of step (iii) to obtain a protein-RNA polynucleotide complex; (v) removing unbound mature crRNA molecule and unbound catalytically inactive crRNA-guided RNA-binding protein; (vi) binding of an antibody to said protein-RNA polynucleotide-complex of step (iv); (vii) removing unbound antibody; and (viii) detecting the antibody-bound protein-RNA polynucleotide-complex of step (vi). The method is suitable for the detection and/or quantification of RNAs and allows to obtain quantifiable results with an improved dynamic range. In addition, the method is advantageously adaptable to RNA molecules with different sequences and can be easily repurposed to automated laboratory platforms or point-of-care type settings. Further benefits include relatively short procedure times, the adaptability to high-throughput immunoassay analyzers and a high specificity.

In a preferred embodiment of the present invention, the catcher polynucleotide is immobilized on magnetic beads or via a streptavidin-biotin binding.

In a particularly preferred embodiment, the target RNA polynucleotide is an mRNA comprising a poly A-tail.

In a further embodiment, the catcher polynucleotide comprises a poly T-section at least partially complementary to the poly-A-tail of the target RNA polynucleotide.

In yet another embodiment, the catcher polynucleotide comprises a segment at least partially complementary to a specific target sequence on the target RNA polynucleotide.

In a further embodiment of the present invention, the complementary section between the catcher polynucleotide and the target RNA polynucleotide comprises between 12 and 30 nucleotides. It is preferred that the complementary section between the catcher polynucleotide and the target RNA polynucleotide comprises 20 nucleotides.

In another embodiment of the present invention, the antibody is specific for the catalytically-inactive crRNA-guided RNA-binding protein. In a preferred embodiment said antibody is a monoclonal antibody.

In another embodiment of the present invention, the catalytically-inactive crRNA-guided RNA-binding protein is a Cas protein.

In a further embodiment, the Cas protein is a member of the family of Cas12 or Cas13 proteins. It is particularly preferred that the Cas protein is a Cas13 protein or a derivative thereof.

In yet another preferred embodiment of the present invention, the detection of the antibody-bound protein-RNA poly-nucleotide complex of step (viii) is based on an enzymatic or a non-enzymatic reaction.

In a specifically preferred embodiment, the enzymatic reaction is an enzymatic reaction of horseradish peroxidase (HRP), alkaline phosphatase (AP), esterase or glucose oxi-dase (GOD), wherein said HRP, AP, esterase or GOD is covalently linked to the antibody.

In a further embodiment, the non-enzymatic reaction is a chemiluminescent reaction of an acridinium ester, wherein said acridinium ester is covalently linked to the antibody.

In yet another preferred embodiment of the method of the present invention, said detection is a quantitative detection or a semi-quantitative detection.

In another aspect the present invention relates to a kit for detecting a target RNA polynucleotide comprising one or more catcher polynucleotides which are complementary to at least a portion of the target RNA polynucleotide, a mature crRNA (CRISPR RNA) molecule which is specific for a target sequence on the target RNA polynucleotide, a cata-lytically-inactive crRNA-guided RNA-binding protein which is guided by said mature crRNA, and an antibody binding to said catalytically-inactive crRNA-guided RNA-binding protein.

In a final aspect, the present invention relates to the use of one or more catcher polynucleotides which are complemen-tary to at least a portion of a target RNA polynucleotide, a mature crRNA (CRISPR RNA) molecule which is specific for a target sequence on the target RNA polynucleotide, and a catalytically-inactive crRNA-guided RNA-binding protein which is guided by said mature crRNA for the detection of a target RNA polynucleotide.

It is to be understood that the features mentioned above and those yet to be explained below may be used not only in the respective combinations indicated, but also in other combinations or in isolation without departing from the scope of the invention.

BRIEF DESCRIPTION OF THE DRAWINGS

FIG. 1 shows a schematic illustration of the steps for detecting a target RNA polynucleotide according to an embodiment of the present invention.

DETAILED DESCRIPTION OF EMBODIMENTS

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respec-tive plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" or "essentially consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "(i)", "(ii)", "(iii)" or "(a)", "(b)", "(c)", "(d)", or "first", "second", "third" etc. and the like in the description or in the claims, are used for distinguishing between similar elements and not necessarily for describing a sequential or chronological order.

It is to be understood that the terms so used are inter-changeable under appropriate circumstances and that the embodiments of the invention described herein are capable of operation in other sequences than described or illustrated herein. In case the terms relate to steps of a method, procedure or use there is no time or time interval coherence between the steps, i.e. the steps may be carried out simul-taneously or there may be time intervals of seconds, min-utes, hours, days, weeks etc. between such steps, unless otherwise indicated.

It is to be understood that this invention is not limited to the particular methodology, protocols etc. described herein as these may vary. It is also to be understood that the terminology used herein is for the purpose of describing particular embodiments only, and is not intended to limit the scope of the present invention that will be limited only by the appended claims.

The drawings are to be regarded as being schematic representations and elements illustrated in the drawings are not necessarily shown to scale. Rather, the various elements are represented such that their function and general purpose become apparent to a person skilled in the art.

Unless defined otherwise, all technical and scientific terms used herein have the same meanings as commonly understood by one of ordinary skill in the art.

As has been set out above, the present invention concerns in one aspect a method of detecting a target RNA polynucle-otide comprising: (i) providing an RNA polynucleotide; (ii) annealing one or more catcher polynucleotides which are complementary to at least a portion of the target RNA polynucleotide to obtain a hybrid of said target RNA poly-nucleotide and said catcher polynucleotide, wherein said catcher nucleotide is immobilized on a surface or connected to a bead; (iii) annealing a mature crRNA (CRISPR RNA) molecule to a specific target sequence on the target RNA polynucleotide; (iv) binding a catalytically-inactive crRNA-guided RNA-binding protein to the complex of step (iii) to obtain a protein-RNA polynucleotide complex; (v) remov-ing unbound mature crRNA molecule and unbound catalyti-cally inactive crRNA-guided RNA-binding protein; (vi) binding of an antibody to said protein-RNA polynucleotide-complex of step (iv); (vii) removing unbound antibody; and (viii) detecting the antibody-bound protein-RNA polynucle-otide-complex of step (vi).

In a first step of the method of the present invention thus an RNA polynucleotide is provided.

As used herein the term "RNA polynucleotide" or "target RNA polynucleotide" relates to any macromolecule com-prising two or more ribonucleotides. Ribonucleotides typi-cally contain a nucleobase, a ribose sugar and at least one phosphate group. The nucleobases are typically adenine, guanine, cytosine and uracil. RNA polynucleotides are typi-cally single-stranded molecules, can, however, also be pro-vided in a double-stranded form by partial complementary base pairing. The RNA polynucleotide typically does not form long double helical stretches. The RNA polynucleotide may be naturally occurring or be artificial. It may comprise, in addition to the elements mentioned above, modifications such as oxidized or methylated nucleotides. The RNA polynucleotide may also, in certain embodiments, comprise artificial additions such as tags or labels.

The RNA polynucleotide may be of any possible origin, e.g. prokaryotic, eukaryotic, archaeal or viral. The RNA polynucleotide to be characterized according to the present invention may have any known possible biological or cellular function. For example it may be any naturally occurring or synthetic polynucleotide such as messenger RNA (mRNA), ribosomal RNA (rRNA), heterogenous nuclear RNA (hnRNA), transfer RNA (tRNA), transfer messenger RNA (tmRNA), micro RNA (miRNA), small nuclear RNA (snRNA), spliced leader RNA (SL RNA), small nucleolar RNA (snoRNA), antisense RNA (asRNA), guide RNA (gRNA), long noncoding RNA (lncRNA), small interfering RNA (siRNA), Piwi-interacting RNA (piRNA), trans-acting RNA (tasiRNA), precursor mRNA (pre-mRNA) or repeat associated siRNA (rasiRNA). The RNA species mentioned typically differ in terms of size, nucleotide composition, folding status and presence or absence of 3' extensions. For example, mRNA molecules in eukaryotes typically comprise a 3' poly-A tail which consists of multiple adenosine monophosphates and is attached to the molecules after transcription by a polyadenylate polymerase. Other RNA species or fragments of eukaryotic mRNAs may not comprise such an elongation. For example, precursor mRNAs (pre-mRNAs) are non-processed mRNA molecules comprising intron sequences which have not yet been modified by the polyadenylate polymerase. In a preferred embodiment, the target RNA polynucleotide is an mRNA, a fragment of an mRNA, pre-mRNA molecule, an ncRNA, a miRNA, an snoRNA, a tmRNA, an siRNA or a piRNA. It is particularly preferred that the target RNA is an RNA polynucleotide which comprises a poly-A tail or an oligo-A tail at the 3' end. Also envisaged are fragments of mRNA polynucleotides which do not comprise the mRNA 3' portion or do not comprise a poly-A tail. Further envisaged are pre-mRNA molecules which typically do not comprise a poly-A tail. Finally, also envisaged are RNA polynucleotide species that do not belong to the group of eukaryotic mRNAs; these species typically do also not comprise poly-A extensions.

The provision of the RNA polynucleotide may include the extraction and/or purification of the RNA molecule, e.g. by guanidine-isothiocyanate lysis, separation from cell debris, filtration, elution from a column, e.g. silica membrane columns, centrifugation, digestion, e.g. DNase digestion, or removal or nucleotide or protein components in a sample etc. It is preferred that the RNA polynucleotide is provided in a buffer solution comprising any suitable ingredient preventing RNA degradation. The buffer may, for example, be an RNAse-free $H_2O$ buffer comprising EDTA (e.g. 0.1 mM) or a TE buffer (10 mM Tris, 1 mM EDTA). The buffer may preferably comprise RNAse blocking compounds or RNase inhibitors such as RNaseZap, Superase, RNaseOUT, ribonuclease inhibitor, RNasin or the like.

The RNA polynucleotide may typically be present in a mixture of other molecules, e.g. of other RNA polynucleotides or other nucleic acids. The other RNA polynucleotides or nucleic acids may have any proportion or be present in any amount, typically in any amount or proportion found in natural situations, e.g. found in cells or samples, or found after typical enrichment steps as mentioned herein.

In further embodiments, the provision of RNA polynucleotides may also include the employment of suitable conditions to keep the RNA molecule or a part of it in a single stranded form. Such conditions may include the use of a certain temperature or range of temperatures before or during the performance of the methods of the invention, and/or the use of specific buffers or salt conditions in order to avoid the formation of secondary structures in the RNA molecule. It is also envisaged that the RNA polynucleotide or a part of it is made single stranded by a short heating denaturation. This short heating denaturing may, for example, be applied when annealing a catcher polynucleotide as described herein.

The provision of RNA polynucleotides may also involve the taking of samples from a subject and their processing, e.g. extraction of RNA or preparatory steps facilitating the extraction of RNA. The term "sample from a subject" as used herein relates to any biological material obtained via suitable methods known to the person skilled in the art from a subject. The sample used in the context of the present invention should preferably be collected in a clinically acceptable manner, more preferably in a way that RNA polynucleotides are preserved. The biological samples may include body tissues and/or fluids, such as blood, or blood components like serum or plasma, sweat, sputum or saliva, semen and urine, as well as feces or stool samples. Furthermore, the biological sample may contain a cell extract derived from or a cell population including an epithelial cell, preferably a neoplastic epithelial cell or an epithelial cell derived from tissue suspected to be neoplastic, or a cancerous cell or cancerous tissue. Alternatively, the biological sample may be derived from the environment, e.g. from the soil, a lake, a river etc., or from animal sources.

In certain embodiments cells may be used as primary sources for RNA polynucleotides. Accordingly, the cells may be purified from obtained body tissues and fluids if necessary, and then further processed to obtain RNA polynucleotides. In certain embodiments samples, in particular after initial processing, may be pooled. The present invention preferably envisages the use of non-pooled samples.

In a specific embodiment of the present invention the content of a biological sample may also be submitted to an enrichment step. For instance, a sample may be contacted with ligands specific for the cell membrane or organelles of certain cell types, functionalized for example with magnetic particles. The material concentrated by the magnetic particles may subsequently be used for the extraction of RNA polynucleotides. In further embodiments of the invention, biopsy or resections samples may be obtained and/or used. Such samples may comprise cells or cell lysates. Furthermore, cells, e.g. tumor cells, may be enriched via filtration processes of fluid or liquid samples, e.g. blood, urine, sweat etc. Such filtration processes may also be combined with enrichment steps based on ligand specific interactions as described herein above.

The RNA polynucleotides are typically provided in a liquid, e.g. aqueous, solution. The solution may comprise or be composed of suitable buffers such as a annealing/hybridization buffer, e.g. comprising SSC, NaCl, sodium phosphate, SDS, TE and/or $MgCl_2$.

In a next step of the method of the invention one or more catcher polynucleotides which are complementary to at least a portion of the target RNA polynucleotide are annealed to the target RNA polynucleotide to obtain a hybrid of said target RNA polynucleotide and said catcher polynucleotide.

The term "annealing a polynucleotide" as used herein relates to the pairing of the single stranded RNA polynucleotide with a complementary single stranded polynucleotide by hydrogen bonds to form a double-stranded polynucleotide. The complementary polynucleotide may either be an RNA molecule or a DNA polynucleotide. It may further comprise one or more modifications such as comprising one or more non-naturally occurring nucleotides, chemical modifications to the nucleotides, the presence of tag or spacer elements etc. It is preferred that the complementary polynucleotide is a DNA polynucleotide or a modified DNA polynucleotide. Nucleotides or nucleotide analogues will bind to their complement under normal conditions, so two complementary strands will bind to each other readily. Annealing can be e.g. performed in a PCR machine or similar heating device which allows to select a predetermined temperature for annealing. If such a heating device allows the application of a temperature gradient across the field of the microtiter plate, an optimal annealing temperature can be quickly determined.

Annealing typically takes place in a liquid solution, e.g. an aqueous solution comprising a suitable buffer as defined above. The annealing may be performed in accordance with any suitable temperature, ion concentration and/or pH parameter known to the skilled person. For example, the annealing may be performed at a temperature and/or pH and/or ionic concentration in the solution at which a complementary base-pairing between most, preferably all complementary bases in the target RNA polynucleotide and the catcher polynucleotide takes place. Unspecific binding or annealing reactions may, for example, be avoided by setting the temperature to a value which only allows for a complete, i.e. 100% complementary binding. Alternatively, the temperature may be set to a value, which allows for a complementary binding of about 99%, 98%, 95%, 90%, 85% or 80% of complementary bases.

The term "complementary", as used herein, refers to the presence of matching base pairs in opposite nucleic acid strands. For example, to a nucleotide or base A in a sense strand a complementary or antisense strand binds with a nucleotide or base T, or vice versa; likewise to a nucleotide or base G in a sense strand the complementary or antisense strand binds with a nucleotide or base C, or vice versa. This scheme of complete or perfect complementarity may, in certain embodiments of the invention, be modified by the possibility of the presence of single or multiple non-complementary bases or stretches of nucleotides within the sense and/or antisense strand(s). Thus, to fall within the notion of a pair of sense and antisense strands, both strands may be completely complementary or may be only partially complementary, e.g. show a complementarity of about 80%, 85%, 90%, 91%, 92%, 93%, 94%, 95%, 96%, 97%, 98%, 99%, 99.5%, or 100% between all nucleotides of both strands or between all nucleotides in specific segments as defined herein. Non-complementary bases may comprise one of the nucleotides A, T, G, C, i.e. show a mismatch e.g. between A and G, or T and C, or may comprise any modified nucleoside bases including, for example, modified bases as described in WIPO Standard ST.25.

The term "complementary to at least a portion of the target RNA polynucleotide" as used herein, means that the annealing segment has a complementary overlap with said target RNA polynucleotide. For example, the catcher polynucleotide may be complementary to a target RNA polynucleotide or a polynucleotide comprising a target specific sequence as defined herein. The overlap may, for example, be an overlap of 5, 7, 10, 12, 15, 18, 20, 22, 25, 28 or 30 nucleotides, or any value in between the mentioned values. Also envisaged are longer overlaps. The overlap typically is at the 3' end of catcher polynucleotide and at the 3' end of the target RNA polynucleotide. Within said overlap the matching or complementarity between the complementary bases is preferably 100%. Alternatively, the matching is less than 100%, e.g. 99%, 95%, 90%, 85% or less than 85%.

The term "catcher polynucleotide", as used herein, relates to a polynucleotide of a defined length which is designed to anneal with and thereby to bind to or to catch a corresponding target RNA polynucleotide. The catcher polynucleotide may have any suitable length. It may, for example, comprise between about 15 to 300 nucleotides, e.g. 15, 16, 17, 18, 19, 20, 21, 22, 23, 24, 25, 26, 27, 28, 29, 30, 40, 50, 100, 150, 200, 250, or 300 nucleotides or any value in between the mentioned values. Also envisaged are longer catcher polynucleotides. It is particularly preferred that the catcher polynucleotide comprises about 15-25 nucleotides. The catcher polynucleotide may, in certain embodiments, further comprise additional elements such as one or more spacer elements, linker elements etc. The catcher polynucleotide may comprise one or more sections which are capable of binding or hybridizing to a target RNA polynucleotide and one or more segments which are not capable of binding or hybridizing to a target RNA polynucleotide. The latter ones may have structural functions or provide a spacer or distancing functionality. It is preferred that the catcher polynucleotide is a single strand DNA molecule. Also envisaged are RNA, PNA, CNA, HNA, LNA or ANA molecules or mixtures thereof as catcher polynucleotide.

The present invention further envisages that the catcher polynucleotide comprises a tag which is capable of binding to a cognate interactor. The interactor-tag binding may advantageously be used to pull said catcher polynucleotides together with any bound or associated RNA polynucleotide from a solution, or to catch a target RNA polynucleotide when moving around said catcher polynucleotide. Examples of suitable tags and interactors are a biotin tag on the catcher polynucleotide and a streptavidin interactor provided on a suitable surface, e.g. of a reaction vessel, or on a bead etc. Further examples include a magnetic bead being bound to a catcher polynucleotide and a magnetic separator attracting said beads, e.g. attached at a surface.

It is preferred that the catcher polynucleotide is immobilized on magnetic beads or via streptavidin-biotin binding.

In a preferred embodiment the catcher polynucleotide comprises a poly T-section at least partially complementary to the poly-A-tail of the target RNA polynucleotide. This type of catcher polynucleotide is specifically designed to bind to or catch a poly-A-segment containing target RNA polynucleotides, in particular an mRNA polynucleotide.

In a further preferred embodiment the catcher polynucleotide comprises a segment at least partially complementary to a specific target sequence on the target RNA polynucleotide. For example, the catcher polynucleotide matches with a predefined sequence stretch on the target RNA polynucleotide. This sequence stretch is typically not a poly-A-tail or segment. The segment may, for example, represent a conserved sequence motif in a specific group of RNA polynucleotides, e.g. 16S RNAs, mitochondrial RNAs etc.

It is envisaged that the complementary section between the catcher polynucleotide and the target RNA polynucleotide, e.g. poly-T/poly-A complementarity or sequence specific complementarity, comprises between 12 to 30 nucleotides, preferably 20 nucleotides.

In a next step a mature crRNA (CRISPR RNA) molecule is annealed to a specific target sequence on the target RNA polynucleotide. The specific target sequence for the crRNA is typically not identical to the specific target sequence for the catcher polynucleotide. It is also preferred that these sequence segments do not overlap.

This method is, in general, based on the employment of the CRISPR/Cas system. The term "CRISPR/Cas system" as used herein relates to a biochemical method to specifically cut and modify nucleic acids, also known as genome editing. For example, genes in a genome can generally be inserted, removed or switched off with the CRISPR/Cas system, nucleotides in a gene or nucleic acid molecule can also be changed. The effect of the concept and activity steps of the CRISPR/Cas system has various similarities to that of RNA interference, since short RNA fragments of about 18 to 20 nucleotides mediate the binding to the target in both bacterial defense mechanisms. In the CRSIPR/Cas system typically RNA-guided nucleic acid-binding proteins, such as Cas proteins, bind certain RNA sequences as ribonucleoproteins. For example, a Cas endonuclease can bind to certain RNA sequences termed crRNA repeats and cut a nucleic acid in the immediate vicinity of these sequences. Without wishing to be bound by theory, it is believed that the crRNA repeat sequence forms a secondary RNA structure and is then bound by the nucleic acid-binding protein (e.g. Cas) which alters its protein folding allowing the target nucleic acid to be bound by the RNA.

In type VI CRISPR/Cas systems a single RNA-guided effector protein, Cas13, forms a crRNA-guided RNA-targeting effector complex when assembled with a crRNA. The CRISPR/Cas13 system accordingly comprises two main components: (i) the programmable single-effector RNA-guided RNase Cas13 and (ii) a 64-66 nucleotide CRISPR RNA (crRNA), which recognizes a 24-30 nucleotide sequence on the target RNA by means of a protospacer-flanking site (PFS). Also, all Cas13 proteins feature two enzymatically distinct ribonuclease activities: (i) nucleolytical processing of pre-crRNA pre-CRISPR-RNA by Cas proteins and/or host factors to generate mature crRNA by RNase and (ii) degradation of target RNA initialized by the RNase activity of two HEPN (higher eukaryotes and prokaryotes nucleotide-binding) domains (Grandaros-Riveron and Aquino-Jarquin, 2018, Cancer Research, 78 (15), 4107-13).

The term "mature crRNA (CRSIPR RNA)" as used herein thus relates to an RNA molecule of the type VI CRISPR/Cas system which is capable of identifying and binding to specific RNA polynucleotide sequences. Typically, the mature crRNA comprises a target specific sequence which can be used to guide an RNA binding protein towards the binding site. This target specific sequence may have any suitable length. It is preferred that said length is between about 19 to 60 nucleotides. More preferably, the sequence has a length of 30 nucleotides.

As described in East-Seletsky et al., 2017, Mol Cell., 66(3), 373-383 mature crRNAs of the type VI CRISPR/Cas system according to the present invention comprise a stem segment, a loop segment, a bulge segment and a spacer segment which comprises the target specific sequence as defined above. Mature crRNAs typically are derived from pre-crRNA molecules via a maturation processing. They can also be provided as such and be used without being derived from said pre-crRNA stage. Further options for obtaining a mature crRNA can be derived from Smargon et al., 2017, Mol Cell., 16, 65(4), 618-630, or from Cox et al., 2017, Science, 10.1126/science.aaq0180. For example, a mature crRNA may be provided which comprises different forms of a stem structure, different loop structures, or in which the spacer sequence is differentially truncated etc. According to further embodiments of the present invention, the sequence and form of the mature crRNA may vary in accordance with the form or identity of the crRNA-guided RNA-binding protein, e.g. Cas protein. Accordingly, depending on the origin of said crRNA-guided RNA-binding protein, a different combination of sequence elements may be used. The present invention further envisages any future development in this context and includes any modification or improvement of the crRNA-RNA-binding protein interaction surpassing the information de-rivable from Smargon et al., 2017, Mol Cell., 16, 65(4), 618-630. Particularly preferred is the use of a mature crRNA for Cas13a, Cas13b, Cas13c or Cas13d. Also envisaged are mature crRNA forms from commercial suppliers, or individually prepared crRNAs.

One of the central principles of the present invention is thus the use of a sequence binding to a target RNA section within the crRNA, wherein said binding sequence is specific for the target RNA polynucleotide and is accordingly able to identify said sequence and to distinguish it from other sequences.

In a further step a catalytically-inactive crRNA-guided RNA-binding protein is bound to the complex of step (iii), i.e. the complex of a mature crRNA (CRISPR RNA) molecule and the target RNA polynucleotide. This results in a protein-RNA polynucleotide complex. In accordance with the CRSPR/Cas approach as defined above, the sequence which has been identified by the mature crRNA as described above is thus indirectly bound (via the crRNA) by a cognate catalytically-inactive crRNA-guided RNA-binding protein.

The term "catalytically-inactive crRNA-guided RNA-binding protein" as used herein relates to an RNA binding protein, e.g. Cas protein, which is capable of binding to a specific stretch of RNA, but does not retain its endonuclease activity and thus does not cut or digest the RNA. This allows for a programmable tracking and identification of RNA molecules without damaging them. In a preferred embodiment, said catalytically-inactive crRNA-guided RNA-binding protein is a Cas protein, more preferably it is a member of the family of Cas12 or Cas13 proteins. Examples of proteins of the Cas12 family include Cas12a. The Cas12 protein is preferably a derivative of the naturally occurring Cas12 protein, in particular a derivative which has been modified, e.g. via protein engineering, to be capable of binding to RNA polynucleotides. It is particularly preferred that it is a Cas13 protein or a derivative thereof. Suitable subtypes may include, for example, Cas13a, Cas13b, Cas13c and Cas13d proteins. Further information on catalytically-inactive crRNA-guided RNA-binding protein may be derived from suitable literature sources such as Cox et al., 2017, Science, 10.1126/science.aaq0180.

Also envisaged are derivatives of the mentioned RNA-binding proteins, e.g. Cas proteins, or mutants thereof. The derivative is preferably a functional derivative of a crRNA-guided RNA-binding protein, which is able to bind to specific stretches of RNA but does no retain its endonuclease activity. In specific embodiments the invention particularly envisages the production of catalytically inactive Cas13 or Cas12 proteins or "dead" Cas proteins (dCas). These proteins can be generated according to any suitable method known to the skilled person. For example, they may be obtained by mutating catalytic arginine residues within the two conserved HEPN domains. Further information may be derived from Abudayyeh et al., 2017, Nature, 550(7675), 280-284.

The present invention also envisages the use of Cas proteins, e.g. Cas13, derived from different bacterial sources. For example, the Cas13 protein may be derived from *Leptotrichia shahii, Leptotrichia wadei, Prevotella* spp., or *Streptococcus pyogenes*.

Further details on the form and use of Cas proteins may be derived from suitable literature sources such as Granados-Riveron and Aquino-Jarquin, 2018, Cancer Research; Cox et al., 2017, Science, 10.1126/science.aaq0180; Gootenberg et al., 2018, Science 360, 439-444 or Abudayyeh et al., 2016, Science, 353 (6299).

In a subsequent step unbound mature crRNA molecules and unbound catalytically inactive crRNA-guided RNA-binding proteins are removed. The removal may be implemented with any suitable technique, e.g. by removing or relocating the reactants, inhibiting or destroying crRNA molecules or RNA binding proteins etc. In a typical and preferred embodiment, the removal is achieved by washing the complex as obtained in the previous step(s) of the method. The washing step may be performed once, or it may be repeated 1, 2, 3 or more times. It is preferred to perform the washing with nuclease-free water or with any other suitable solution containing appropriate ion concentration and/or having a suitable pH, as would be known to the skilled person.

In a further step of the method according to the present invention, an antibody binds to the protein-RNA polynucleotide complex of step (iv).

The term "antibody" as used herein refers to immunoglobulin molecules and immunologically active portions of immunoglobulin molecules, i.e. molecules that contain an antigen binding site that immunospecifically binds an antigen, in particular specifically binds the protein-RNA polynucleotide complex as defined herein above, more specifically binds the catalytically inactive crRNA-guided RNA-binding protein being part of said complex. The immunoglobulin molecules of the invention can be of any type (e.g., IgG, IgE, IgM, IgD, IgA and IgY), class (e. g., IgG1, IgG2, IgG3, IgG4, IgA1 and IgA2) or subclass of immunoglobulin molecule. The immunospecific binding refers to the immunospecific detection and binding of an antibody to an antigenic epitope of a catalytically inactive crRNA-guided RNA-binding protein as defined herein above. In further embodiments antibodies of the invention include polyclonal, monoclonal, multispecific, human, humanized or chimeric antibodies, or whole immunoglobulin molecules.

It is preferred that the antibody is a monoclonal antibody. In a particularly preferred embodiment, the antibody according to the present invention is a monoclonal antibody capable of binding a catalytically inactive dCas13 protein.

The antibody may, in certain embodiments, also be or comprise an antibody substructure. The term "antibody substructure" as used herein refers to single chain antibodies, Fab fragments, Fab' fragments, fragments produced by a Fab expression library, F(ab')2, Fv, disulfide linked Fv, minibodies, diabodies, scFv, sc(Fv)2, and epitope-binding fragments of any of the above. Preferred are Fab, Fab' and F(ab')2, Fv, single-chain Fvs (scFv), sc(Fv)2, single-chain antibodies, disulfide-linked Fvs (sdFv) and fragments comprising either a VL or VH domain. The term "Fab fragment" as used herein refers to antibody fragments consisting of the first constant domain of the heavy chain (CH1), the constant domain of the light chain (CL), the variable domain of the heavy chain (VH) and the variable domain of the light chain (VL) of an intact immunoglobulin protein.

The term "F(ab')2" or "F(ab')2 fragment" as used herein refers to antibody fragments consisting of two first constant domains of the heavy chain (CH1), two constant domains of the light chain (CL), two variable domains of the heavy chain (VH) and two variable domains of the light chain (VL) of an intact immunoglobulin protein, i.e. it comprises two Fab fragments. Additionally, F(ab')2 molecules comprise a S-S linkage in the antibody hinge region which combines the Fab fragments. The term "Fab' fragment" as used herein refers to fragments derived from "F(ab')2" molecules, preferably fragments comprising the S-S linkage in the antibody hinge region. The term "Fv fragments" as used herein refers to antibody fragments consisting of the two variable antibody domains VH and VL; further details may be derived from Skerra and Pluckthun, 1988, Science, 240: 1038-1041. The term "single chain Fv fragment (scFv)" as used herein relates to antibody fragments consisting of the two VH and VL domains linked together by a flexible peptide linker; further details may be derived from Bird and Walker, 1991, Trends Biotechnol., 9: 132-137.

Also envisaged are antibody forms such as diabodies or mini-bodies. Details may be derived from Hudson and Kortt, 1999, J. Immunol. Methods, 231(1-2):177-89 or Quiocho, 1993, Nature, 362(6418): 293-294.

The antibodies may be from any animal origin including birds and mammals. Preferably, the antibodies are murine (e.g., mouse and rat), donkey, monkey, rabbit, goat, guinea pig, camel, horse, chicken, or human.

The antibodies according to the present invention are typically monospecific. In certain specific embodiments, the antibody may also be bispecific, or of a greater multispecificity. Multispecific antibodies may be specific for different epitopes of a catalytically inactive crRNA-guided RNA-binding protein as defined herein above.

Antibodies of the present invention may also be described or specified in terms of the epitope(s) or portion(s) of a polypeptide which they recognize or specifically bind. The epitopes may preferably be present on a catalytically inactive crRNA-guided RNA-binding protein as defined herein above, more preferably on a catalytically inactive Cas12 or Cas13 protein, or a catalytically inactive Cas12a derivative capable of binding to RNA polynucleotides, or a catalytically inactive Cas13a, Cas13b, Cas13c or Cas13d protein.

In a further step of the method of the present invention, unbound antibodies are removed. The removal may be implemented with any suitable technique. In a typical and preferred embodiment, the removal is achieved by washing the antibody-bound complex as obtained in the previous step(s) of the method. The washing step may be performed once, or it may be repeated 1, 2, 3 or more times. It is preferred to perform the washing with nuclease-free water or with any other suitable solution containing appropriate ion concentration and/or having a suitable pH, as would be known to the skilled person.

In a final step of the method of the present invention, the antibody-bound protein-RNA polynucleotide-complex as mentioned above is detected. The detection may be performed according to any suitable methodology known to the skilled person. The detection of the antibody-bound protein-RNA polynucleotide-complex as mentioned above is preferably based on an enzymatic reaction or a non-enzymatic reaction.

The non-enzymatic reaction may, for example, be performed via the identification of a label present on the antibody as defined herein. Such a label may, for example be any suitable label known to the skilled person, e.g. a radioactive label, a fluorescent label, a chemiluminescent label or a bioluminescent label. Examples of labels that can be conjugated to an antibody according to the invention include fluorescent dyes or metals (e.g. fluorescein, rhodamine, phycoerythrin, fluorescamine), chromophoric dyes (e.g. rhodop-sin), chemiluminescent compounds (e.g. luminal, imidazole), fluorescent polypeptides (e.g. green fluorescent protein (GFP)) and bioluminescent proteins (e.g. luciferin, luciferase), and contrast agents such as USPIOS or 19Fluor. Further labels which may be used within the context of the present invention include 6-FAM, HEX, TET, ROX, Cy3, Cy5, Texas Red or Rhodamine, TAMRA, Dabcyl, Black Hole Quencher, BHQ-1 or BHQ-2. The antibody may also be labeled with radioisotopes e.g. $^3$H, $^{14}$C, $^{32}$P, $^{33}$P, $^{35}$S, $^{125}$I, $^{11}$C, $^{13}$N, $^{15}$O, $^{18}$F, $^{64}$Cu, $^{62}$Cu, $^{124}$I, $^{76}$Br, $^{82}$Rb, $^{68}$Ga or $^{18}$F. Particularly preferred is a chemiluminescent detection.

More preferably, the detection is based on a chemiluminescent reaction of an acridinium ester. In general, acridinium esters can be stimulated to produce light in the presence of dilute alkaline hydrogen peroxide. Moreover, formed N-methylacridone molecules are typically resistant to quenching before radiation. The chemiluminescent label, in particular the acridinium ester, may be conjugated or covalently linked to the antibody as described herein at any suitable position.

The detection of the antibody-bound protein-RNA polynucleotide-complex as mentioned above via an enzymatic reaction may involve the presence of an enzymatic label. Preferred enzymatic activities or labels are horseradish peroxidase (HRP), alkaline phosphatase (AP), glucose oxidase (GOD) or esterase. The enzymatic activities may accordingly be conjugated or covalently linked to the antibody as described herein at any suitable position.

The enzyme-based detection further requires a suitable substrate which is converted by an enzymatic activity as mentioned above. For example, for horseradish peroxidase (HRP) there are several different types of substrates which may be chosen in accordance with the particular assay and mode of detection. One option is the use of chromogenic HRP substrates, which remain in solution and become colored after reaction with HRP. Typically used chromogenic HRP substrates include 3,3',5,5'-tetramethylbenzidine (TMB) and 2,2'-azino-di-[3-ethylbenzthiazoline-6-sulfonic acid](ABTS). After oxidation by HRP, some substrates precipitate. An oxidized HRP substrate may, for example, form a precipitate that is colored, electron-dense, or luminescent. An example of a suitable HRP substrate that is both, colored and electron-dense, which is envisaged by the present invention, is 3,3'-diaminobenzidine (DAB). Further envisaged is the use of the enhanced chemiluminescence (ECL) technology, e.g. as commercialized by BioRad Inc.

Suitable substrates for alkaline phosphatase (AP) include p-Nitrophenyl phosphate (PNPP) and 4-Methylumbelliferyl phosphate (4-MUP). The use of PNPP is based on the principle that when alkaline phosphatase and PNPP are reacted, a yellow water-soluble reaction product is formed. This reaction product can be detected since it absorbs light at 405 nm. 4-MUP is a substrate for alkaline phosphatase that forms the soluble fluorescent reaction product methylumbelliferone. Fluorescence can be measured with excitation at 360 nm and emission at 440 nm. The fluorescent end product may, for example, be observed using a UV light source.

The enzymatic test with glucose oxidase (GOD} is based on the oxidation of glucose by glucose oxidase, i.e. the oxygen-dependent oxidation of the C1 carbon atom of glucose, resulting in the provision of gluconolactone and hydrogen peroxide. Hydrogen peroxide may subsequently be reduced in a downstream color reaction performed by a peroxidase (POD) such as HRP. Alternatively, the produced hydrogen peroxide may be measured electrochemically and thus be quantified.

Suitable substrates for esterase based tests include 5-Bromo-4-chloro-3-indolyl acetate, 4-Methylumbelliferyl acetate, 1-Naphthyl acetate, 1-Naphthyl butyrate, 4-Nitrophenyl dedecanoate, 4-Nitrophenyl myristate, 4-Nitrophenyl butyrate p-aminophenylbutyrate, 5-(and 6-)carboxy-2',7'-dichlorofluorescein diacetate or 4-Nitrophenyl octanoate.

The detection may be performed according to any suitable assay format, in particular an immunobiological assay. Examples of envisaged immunobiological assays in which the target RNA polynucleotide according to the present invention may be used include competitive and non-competitive assay systems using techniques such as western blots, radioimmunoassay like RIA (radio-linked immunoassay), ELISA (enzyme linked immunosorbent assay), "sandwich" immunoassays, immunoradiometric assays, fluorescent immunoassays, e.g. FIA (fluorescence-linked immunoassay), chemiluminescence immunoassays and electrochemiluminescence immunoassay (ECLIA) or suitable derivatives thereof. Details and further features of such assays would be known to the skilled person or can be derived from suitable literature sources such as the ebook Assay Guidance Manual, edited by G. Sitta Sittampalam, Bethesda (MD): Eli Lilly & Company and the National Center for Advancing Translational Sciences; 2004 at ncbi.nlm.nih.gov/books/NBK53196/, in particular section Immunoassay Methods, Karen L. Cox et al., Eli Lilly & Company, Indianapolis, IN, of 2012, or later updated versions thereof. In specific embodiments, the assay format is an ELISA. The term "ELISA" or "ELISA assay" as used herein relates to a solid-phase enzyme immunoassay (EIA) which is generally used to detect the presence of a compound in a sample, which is typically liquid, or has been brought into solution, using one or more antibodies. The ELISA can be used as a diagnostic tool, e.g. in medicine, or as quality-control check.

Typically, antigens from the sample, i.e. antigens present on the catalytically-inactive crRNA-guided RNA-binding protein bound to the target RNA polynucleotide as described herein, are attached to a solid phase such as a surface or a magnetic bead which can be attracted to a compatible surface, e.g. via the binding of the RNA polynucleotide to the catcher polynucleotides which is complementary to at least a portion of a target RNA polynucleotide as described herein above. It is preferred to use magnetic beads. Subsequently, a specific antibody is applied over the surface or the beads so it can bind to the antigen. This antibody may be linked to an enzyme, e.g. as defined herein above, and, in the final step, a substance containing the enzyme's substrate is added. The subsequent reaction produces a detectable signal, for example a color change in the substrate.

In particularly preferred embodiments the assay is performed in accordance with and/or on immunoassay platforms such as Centaur or Atellica as commercialized by Siemens Healthineers. Further information on these platforms may be derived, for example, from healthcare.siemens.de/immunoassay/systems/advia-centaur-xpt (visited on Oct. 24, 2018) or healthcare.siemens.com/integrated-chemistry/systems/atellica-solution-analyzers (visited on Oct. 24, 2018), or from the document "ADVIA Centaur XPT Immunoassay System Technical Specifications" which can be derived from suitable internet repositories such as https://static.healthcare.siemens.com/siemens_hwem-hwem_ssxa_websites-context-root/wcm/idc/groups/public/@global/@lab/documents/download/m da2/otmw/~edisp/170168-gc1_updates_advia_centaur_xpt_ss_fnl2-03931885.pdf (visited on Oct. 25, 2018) or from the document "Atellica IM 1300 Analyzer and Atellica IM 1600

Analyzer Technical Specifica-tions" which can be derived from suitable internet repositories such as https://static.healthcare.siemens.com/siemens_hwem-hwem_ssxa_web-sites-context-root/wcm/idc/groups/public/@global/@lab/@corelab/documents/d ownload/mda4/mtgy/~edisp/30-17-10702-01-76_atellica_im_1300-1600_ss_final_v2-05269699.pdf (visited on Oct. 25, 2018).

The detection according to the present invention may be a qualitative detection, a semi-quantitative detection or a quantitative detection.

The term "qualitative detection" as used herein means that the method of the present invention is capable of indicating whether a specific target RNA polynucleotide is present or not. Accordingly, by detecting a signal via the bound antibody, it can de deduced that the target RNA polynucleotide is present, e.g. in a mixture of different RNA polynucleotides as described above. In the preferably envisaged ELISA a qualitative assay means that the assay can be used to achieve a yes or no answer indicating whether a target RNA polynucleotide (via the catalytically-inactive crRNA-guided RNA-binding protein as defined herein above) is present in a sample. This may be achieved via a comparison versus a sample containing no target RNA polynucleotide or an unrelated control target RNA polynucleotide.

The term "semi-quantitative detection" as used herein means that the method of the present invention is capable of indicating whether a specific target RNA polynucleotide is present above a certain threshold with respect to its numbers or amount or concentration in a solution. The threshold may be suitably defined as would be known to the skilled person. For example, by detecting a signal in an assay on the basis of the antibody as described herein, it can de deduced that the target RNA polynucleotide which is present, e.g. in a mixture of different RNA polynucleotides as described above, has surpassed a certain predefined limit with respect to its numbers, amount or concentration. The format also allows to compare relative levels of target RNA polynucleotides between samples, in particular between samples used within the same assay format, e.g. ELISA, or assays performed on the platforms Centaur or Atellica as mentioned herein above.

The term "quantitative detection" as used herein means that the method of the present invention is capable of indicating the approximate or exact numbers, amount or concentration of a specific target RNA polynucleotide used for the method. For the quantitative detection suitable control and/or calibration steps are required. Typically, the quantitative de-tection involves the interpretation of signals in comparison to a standard curve (e.g. a serial dilution of a known, purified target RNA polynucleotide) in order to precisely calculate the concentrations of target RNA polynucleotide in various samples. For example, in an ELISA format, the signal data obtained may be graphed with optical density vs. log concentration to produce a sigmoidal curve. Known concentrations of target RNA polynucleotide may be used to produce a standard curve. This data may subsequently be used to measure the concentration of unknown samples by comparison to the linear portion of the standard curve. This can advantageously be done directly on the graph or with suitable curve fitting software known to the skilled person.

It is further preferred that the quantitative detection is performed by averaging the triplicate of the standards readings and by deducting the reading of the blank control sample. Subsequently, a standard curve is plotted and the line of best fit is identified so that the concentration of the samples can be determined. Any dilutions made need to be adjusted for at this stage. Alternatively, the signal data may be plotted using semi-log, log/log, log/logit or derivatives thereof in 4 or 5 parameter logistic models. Using software based/automated solutions suitable graphing approaches may be implemented. The approach further envisages the use of linear regression, e.g. within a software package, which allows for additional control possibilities. Further details would be known to the skilled person or can be derived from suitable literature sources such as the document Laboratory Procedure Manual: Complex PSA using Advia Centaur in Serum NHANES 2007-2008 of the University of Washington Medical Centre.

In very specific embodiments detected target RNA polynucleotides, i.e. RNA polynucleotides comprising a target specific sequence, may subsequently be extracted, optionally be purified, stored and/or used for additional activities.

The present invention further envisages, in specific embodiments, the optional use or implementation of one or more additional washing or removal steps between or after any one or more of the above mentioned steps as mentioned above. These removal steps may be implemented with any suitable technique, e.g. by removing or relocating the reactants, inhibiting or destroying molecules. In a typical and preferred embodiment, the removal is achieved by washing as described herein above. The washing step may be performed once, or it may be repeated 1, 2, 3 or more times. It is preferred to perform the washing with nuclease-free water or with any other suitable solution containing appropriate ion concentration and/or having a suitable pH, as would be known to the skilled person.

In preferred embodiments, one or more of the removal or washing steps as mentioned herein above, including the removal steps for the unbound mature crRNAs, unbound catalytically inactive crRNA-guided RNA-binding protein or the unbound antibodies, may be carried out with the help of a magnet capable of collecting magnetic beads, e.g. connected to the target RNA polynucleotide as mentioned above. The beads may subsequently be washed with a continuous water flow, followed by the creation of vacuum which removes the water.

It is particularly preferred that the washing steps, including any washing step as mentioned herein above, are performed in accordance with procedures described for the Centaur or Atellica assay platforms of Siemens Healthineers as described herein above or known to the skilled person.

In a further aspect the present invention relates to a kit comprising one or more catcher polynucleotides which are complementary to at least a portion of the target RNA polynucleotide, a mature crRNA (CRISPR RNA) molecule which is specific for a target sequence on the target RNA polynucleotide, a catalytically-inactive crRNA-guided RNA-binding protein which is guided by said mature crRNA, and an antibody binding to said catalytically-inactive crRNA-guided RNA-binding protein. The kit is preferably used for detection of a target RNA polynucleotide, e.g. in a mixture of RNA polynucleotides. The features of the methods as defined herein above apply also to the kit of the present invention. The kit may, for example, comprise reagents and components as defined in one or more steps of the present methods. The kit may, in general, comprise suitable buffer solutions, labels or washing liquids etc. The kit may also comprise suitable substrates for the detection of the bound antibody, e.g. enzymatic substrates as defined herein above, or substrates for non-enzymatic detection as described herein above. Furthermore, the kit may comprise an amount of a known nucleic acid molecule, e.g. RNA polynucleotide or protein, which can be used for a calibration of the kit or as an internal control. Corresponding ingredients would be known to the skilled person.

Additionally, the kit may comprise an instruction leaflet and/or may provide information as to its usage etc.

Also envisaged is an apparatus performing the above mentioned method steps. The apparatus may, for example, be composed of different modules which can perform one or more steps of the method of the present invention. These modules may be combined in any suitable fashion, e.g. they may be present in a single place or be separated. Also envisaged is the performance of the method at different points in time and/or in different location. Some steps of the method as defined herein may be followed by breaks or pauses, wherein the reagents or products etc. are suitably stored, e.g. in a freezer or a cooling device. In case these steps are performed in specific modules of an apparatus as defined herein, said modules may be used as storage vehicle. The modules may further be used to transport reaction products or reagents to a different location, e.g. a different laboratory etc.

In a further aspect the present invention relates to the use of one or more catcher polynucleotides which are complementary to at least a portion of a target RNA polynucleotide, a mature crRNA (CRISPR RNA) molecule which is specific for a target sequence on the target RNA polynucleotide, and a catalytically-inactive crRNA-guided RNA-binding protein which is guided by said mature crRNA for the detection of a target RNA polynucleotide. The use is preferably for an RNA polynucleotide detection assay. The assay may comprise, for example, the step of binding a catcher polynucleotide which is complementary to at least a portion of a target RNA polynucleotide to said target RNA polynucleotide, the step of binding a mature crRNA (CRISPR RNA) molecule which is specific for a target sequence to the target RNA polynucleotide, and the step of binding air guiding a catalytically-inactive RNA-binding protein to the target sequence via the mature crRNA. In further embodiments, the present invention also envisages the use of an antibody as defined herein above, for the detection of a bound catalytically-inactive crRNA-guided RNA-binding protein as described above. The assay may accordingly also comprise the antibody binding and subsequent detection step as outlined above. The features of the methods as defined herein above apply also to the use or assay as mentioned above Turning now to FIG. 1, a schematic illustration of the steps for an assay for detecting a target RNA polynucleotide according to an embodiment of the present invention is provided. In a first step a target RNA polynucleotide 1 and a catcher polynucleotide with a poly T-strand 2 which is bound to a bead 11 are provided. The catcher polynucleotide with a poly T-strand 2 and bound to a bead 11 is annealed 3 to the target RNA polynucleotide 1. Subsequently, a mature crRNA (CRISPR RNA) molecule 4 is bound 6 to a specific target sequence on the target RNA polynucleotide 1, followed by binding 6 of a catalytically-inactive crRNA-guided RNA-binding protein 5. This results in a protein-RNA polynucleotide complex 7. In a subsequent step, an antibody comprising a label 9 binds 8 to the protein-nucleic acid-complex 7, in particular the catalytically-inactive crRNA-guided RNA-binding protein 5. Finally, the bound antibody 10 can be detected.

LIST OF REFERENCE NUMERALS

1 Target RNA polynucleotide with poly A-tail (SEQ ID NO: 1)

2 Catcher polynucleotide with a poly T-section (SEQ ID NO: 2) complementary to the poly A-tail of the target RNA polynucleotide

3 Annealing of catcher polynucleotide to target RNA polynucleotide

4 Mature crRNA (CRISPR RNA) Catalytically-inactive crRNA-guided RNA-binding protein

6 Annealing of mature crRNA to a target sequence on the target RNA polynucleotide and binding of catalytically-inactive crRNA-guided RNA-binding protein to the crRNA-target RNA polynucleotide-complex

7 Protein-RNA polynucleotide complex

8 Binding of an antibody to the protein-nucleic acid-complex

9 Antibody specific for catalytically-inactive crRNA-guided RNA-binding protein

10 Antibody bound to the protein-RNA polynucleotide-complex

11 Bead

The following example and FIGURE are provided for illustrative purposes. It is thus understood that the figures are not to be construed as limiting. The skilled person in the art will clearly be able to envisage further modifications of the principles laid out herein.

EXAMPLES

Example 1

The mRNA immunoassay presented is a two-step nucleic acid capture immunoassay adapted to the ADVIA Centaur® Immunoassay System (Siemens Healthcare Diagnostics, Tarrytown, NY). This immunoassay analyzer platform is present in clinical laboratories worldwide and can be used to measure a myriad of protein and small molecule analytes by respective assays using acridinium ester technology. The components of the assay prototype consist of the solid phase (containing streptavidin linked micro particles), a biotinylated catcher oligo nucleotide (poly-T catcher) that is complementary to a complete mRNA species with poly-A tail, a crRNA guided inactive cas13a protein which recognizing a specific mRNA and finally a monoclonal antibody to inactive Cas13a labeled with acridinium ester.

In the assay, the purified mRNA from a blood sample is first hybridized to the biotinylated poly-T catcher polynucleotide, generating perfectly matched DNA/RNA heterohybrids. In a second step, these biotinylated DNA/RNA heterohybrids are then incubated with and bound to the streptavidin-labeled solid phase and recognized by a crRNA guided inactive Cas13a protein. In the next step, the acridinium ester-labeled antibody to inactive Cas13a protein is added. The amount of antibody bound will therefore be proportional to the amount of mRNA recognized by crRNA guided inactive Cas13a protein present in the reaction, which again is proportional to the amount of that specific mRNA species present in the blood sample. Chemiluminescence is then triggered by subsequent addition of an acid and base reagent.

In detail, the following nine steps are carried out by the ADVIA Centaur system in an automated manner:

1) Pipetting 75 μl samples in a cuvette. 2) Pipetting 75 μl reagent (20 mmol/L sodium phosphate pH 7.2, 300 mM NaCl, 0.1% Triton X-100, 0.5% bovine serum albumin, 0.02% sodium azide) containing biotinylated polyT catcher oligo nucleotides (10 nmol/L) and incubation for 6 minutes at 37° C. 3) Pipetting 150 μl solid phase, a crRNA guided inactive cas13a protein and incubating for 18 minutes at 37° C. 4) Separation of solid phase from the mixture and removing the liquid phase. 5) Washing the cuvette with washing solution I and incubation for 6.75 minutes at 37° C. 6) Pipetting 95 µl antibody reagent and incubation for 18 minutes at 37° C. 7) Separation of solid phase from the mixture and removing the liquid phase. 8) Washing the cuvette with washing solution I. 9) Pipetting 300 µl reagent A (acid) and 300 µl reagent B (base), respectively to generate a chemiluminescence signal.

Calibration curves and calculation of concentrations: The calibration curve is measured with synthetic mRNAs from a concentration of 1 pmol/L to 1 nmol/L on an ADVIA Centaur system, carrying out a second-degree polynomial analysis to determine the equation of the relationship between RLU (relative light unit) counts and mRNA concentration. The biological samples are then measured on the same ADVIA Centaur system.

The concentration of a certain mRNA of biological samples is calculated from the RLU counts based on the equation of the calibration curve.

(vi) detecting the antibody-bound protein-RNA polynucleotide complex of step (v).

2. The method of claim 1, wherein the catcher polynucleotide is immobilized on magnetic beads or via a streptavidin-biotin binding.

3. The method of claim 1, wherein the target RNA polynucleotide is an mRNA comprising a poly A-tail.

4. The method of claim 1, wherein the target RNA polynucleotide comprises a poly-A-tail and the catcher polynucleotide comprises a poly T-section at least partially complementary to the poly-A-tail of the target RNA polynucleotide.

5. The method of claim 1, wherein the catcher polynucleotide comprises a segment at least partially complementary to a specific target sequence on the target RNA polynucleotide.

6. The method of claim 4, wherein the complementary section between the catcher polynucleotide and the target RNA polynucleotide comprises between 12 to 30 nucleotides.

---

---

The invention claimed is:

1. A method for detecting a target RNA polynucleotide, comprising the following steps:
(i) annealing one or more catcher polynucleotides which are complementary to at least a portion of the target RNA polynucleotide to obtain a hybrid of the target RNA polynucleotide and the catcher polynucleotide, wherein the catcher polynucleotide is immobilized on a surface or connected to a bead;
(ii) annealing a mature crRNA (CRISPR RNA) molecule to a specific target sequence on the target RNA polynucleotide of the hybrid of the target RNA polynucleotide and the catcher polynucleotide to form a complex;
(iii) binding a catalytically-inactive crRNA-guided RNA-binding protein to the complex of step (ii) to obtain a protein-RNA polynucleotide complex;
(iv) removing unbound mature crRNA molecule and unbound catalytically inactive crRNA-guided RNA-binding protein;
(v) binding an antibody to the protein-RNA polynucleotide complex of step (iii); and 7. The method of claim 1, wherein the antibody is specific for the catalytically-inactive crRNA-guided RNA-binding protein.

8. The method of claim 1, wherein the catalytically-inactive crRNA-guided RNA-binding protein is a Cas protein.

9. The method of claim 8, wherein the Cas protein is a member of the family of Cas12 or Cas13 proteins.

10. The method of claim 1, wherein the detection of the antibody-bound protein-RNA polynucleotide-complex of step (vi) is based on an enzymatic reaction or a non-enzymatic reaction.

11. The method of claim 10, wherein the enzymatic reaction is an enzymatic reaction of horseradish peroxidase (HRP), alkaline phosphatase (AP), esterase or glucose oxidase (GOD), wherein the HRP, AP, esterase or GOD is covalently linked to the antibody.

12. The method of claim 10, wherein the non-enzymatic reaction is a chemiluminescent reaction of an acridinium ester, wherein the acridinium ester is covalently linked to the antibody.

13. The method of claim 1, wherein the detection is a quantitative detection or a semi-quantitative detection.

14. The method of claim 4, wherein the complementary section between the catcher polynucleotide and the target RNA polynucleotide comprises 20 nucleotides.

15. The method of claim 1, wherein the antibody is a monoclonal antibody.

16. The method of claim 8, wherein the Cas protein is a Cas13 protein or a derivative thereof.

17. The method of claim 1, wherein the target RNA polynucleotide and/or the catcher polynucleotide comprises naturally occurring nucleotides or one or more modified nucleotides.

18. The method of claim 17, wherein the one or more modified nucleotides comprise oxidized nucleotides, methylated nucleotides, or labeled nucleotides.

19. A method for detecting a target RNA polynucleotide, comprising the following steps:

(i) annealing a catcher polynucleotide to the target RNA polynucleotide to obtain a hybrid of the target RNA polynucleotide and the catcher polynucleotide, wherein the catcher polynucleotide is immobilized on a surface or connected to a bead and comprises a segment that is at least partially complementary to a portion of the target RNA polynucleotide and a poly T-section that is at least partially complementary to a poly-A-tail of the target RNA polynucleotide, (ii) annealing a mature crRNA (CRISPR RNA) molecule to a specific target sequence on the target RNA polynucleotide to form a complex;

(iii) binding a catalytically-inactive crRNA-guided RNA-binding protein to the complex of step (ii) to obtain a protein-RNA polynucleotide complex;

(iv) removing unbound mature crRNA molecule and unbound catalytically inactive crRNA-guided RNA-binding protein;

(v) binding an antibody to the protein-RNA polynucleotide complex of step (iii); and (vi) detecting the antibody-bound protein-RNA polynucleotide complex of step (v).

* * * * *

SEQUENCE LISTING

```
<160> NUMBER OF SEQ ID NOS: 2

<210> SEQ ID NO 1
<211> LENGTH: 13
<212> TYPE: DNA
<213> ORGANISM: Artificial Sequence
<220> FEATURE:
<223> OTHER INFORMATION: synthetic construct

<400> SEQUENCE: 1
aaaaaaaaaa aaa                                                    13

<210> SEQ ID NO 2
<211> LENGTH: 13
<212> TYPE: DNA
<213> ORGANISM: Artificial Sequence
<220> FEATURE:
<223> OTHER INFORMATION: synthetic construct

<400> SEQUENCE: 2
tttttttttt ttt                                                    13
```